United States Patent
Campbell

(10) Patent No.: US 9,078,718 B2
(45) Date of Patent: Jul. 14, 2015

(54) PLATING SYSTEMS FOR BONE FIXATION

(75) Inventor: Christopher M. Campbell, Temecula, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 1565 days.

(21) Appl. No.: 11/771,383

(22) Filed: Jun. 29, 2007

(65) Prior Publication Data

US 2008/0097443 A1 Apr. 24, 2008

Related U.S. Application Data

(60) Provisional application No. 60/818,029, filed on Jun. 30, 2006, provisional application No. 60/818,030, filed on Jun. 30, 2006.

(51) Int. Cl.
| | | |
|---|---|---|
| *A61B 17/88* | (2006.01) | |
| *A61B 17/80* | (2006.01) | |
| *A61B 17/70* | (2006.01) | |
| *A61B 17/86* | (2006.01) | |
| *A61B 17/00* | (2006.01) | |

(52) U.S. Cl.
CPC .............. *A61B 17/88* (2013.01); *A61B 17/7059* (2013.01); *A61B 17/8033* (2013.01); *A61B 17/8042* (2013.01); *A61B 17/8023* (2013.01); *A61B 17/8635* (2013.01); *A61B 2017/00862* (2013.01); *A61B 2017/00867* (2013.01)

(58) Field of Classification Search
CPC ........... A61B 17/7059; A61B 17/8023; A61B 17/8033; A61B 17/8042; A61B 17/88
USPC ................... 606/60, 70–71, 86 A, 86 B, 104, 606/280–289, 304, 902–907, 915
See application file for complete search history.

(56) References Cited

U.S. PATENT DOCUMENTS

| | | | |
|---|---|---|---|
| 6,361,537 B1 * | 3/2002 | Anderson | 606/86 B |
| 6,602,255 B1 * | 8/2003 | Campbell et al. | 606/290 |
| 6,652,525 B1 * | 11/2003 | Assaker et al. | 606/296 |
| 7,322,984 B2 * | 1/2008 | Doubler et al. | 606/70 |
| 2003/0225409 A1 * | 12/2003 | Freid et al. | 606/69 |
| 2004/0097940 A1 * | 5/2004 | Paul | 606/69 |
| 2004/0133205 A1 * | 7/2004 | Thramann et al. | 606/69 |
| 2004/0181226 A1 * | 9/2004 | Michelson | 606/61 |
| 2005/0010227 A1 * | 1/2005 | Paul | 606/71 |
| 2005/0010277 A1 * | 1/2005 | Chuter | 623/1.13 |
| 2005/0059970 A1 * | 3/2005 | Kolb | 606/69 |
| 2005/0137597 A1 * | 6/2005 | Butler et al. | 606/69 |
| 2005/0149027 A1 | 7/2005 | Campbell et al. | |
| 2006/0079901 A1 * | 4/2006 | Ryan et al. | 606/69 |
| 2006/0235398 A1 * | 10/2006 | Farris et al. | 606/69 |
| 2006/0247639 A1 * | 11/2006 | Anderson | 606/69 |

FOREIGN PATENT DOCUMENTS

| | | |
|---|---|---|
| WO | WO 2005/006997 A | 1/2005 |
| WO | WO 2006/119242 A | 11/2006 |

OTHER PUBLICATIONS

International Search Report for Application No. PCT/US2007/015228 8 dated Mar. 19, 2008.

* cited by examiner

*Primary Examiner* — Larry E Waggle, Jr.
(74) *Attorney, Agent, or Firm* — Michael J. Loi

(57) ABSTRACT

The present invention provides systems and methods for bone fixation, and in particular, systems and methods for fusion of human cervical spine from the anterior aspect. To that end, some of the embodiments of the invention are directed to plate systems for aligning and maintaining adjacent cervical vertebrae in a selected spatial relationship during spinal fusion of such vertebrae.

16 Claims, 10 Drawing Sheets

PLATING SYSTEMS FOR BONE FIXATION

RELATED APPLICATIONS

This application claims the benefit of priority from U.S. Ser. No. 60/818,029, filed on Jun. 30, 2006 and U.S. Ser. No. 60/818,030, filed on Jun. 30, 2006 both of which are incorporated herein by reference in their entireties.

BACKGROUND OF THE INVENTION

An increasingly accepted procedure for treating spinal disorders involves using substantially rigid plates to hold vertebrae in desired spatial relationships and orientations relative to each other. The upper cervical spine can be approached anteriorly or posteriorly, although anterior approaches are of more interest in connection with this invention. In either case, holes are drilled and tapped in at least two of the vertebrae, to receive screws or other fasteners used to secure the plate. The holes are accurately positioned with reference to openings formed through the cervical plate. In some cases the screws may be self-tapping. Typically the plate is curved about its longitudinal axis to facilitate contiguous surface engagement of the plates with the vertebrae. With the plate maintained against the vertebrae, the fasteners are secure within the holes. As a result, the plate maintains the attached vertebrae in a desired spacing and orientation with respect to each other.

One of the problems associated with this technique is the tendency of screws or other fasteners to gradually work loose after fixation. Slight shock or vibration of the vertebrae, due to walking, climbing stairs or more vigorous activity by the patient following treatment increases this tendency, jeopardizing the integrity of fixation. Moreover, as the fasteners work loose, the outward protrusion of the heads over other components of the fasteners can be a source of discomfort and present the risk of trauma to adjacent and surrounding soft tissue.

The curvature of cervical plates typically results in a convergence of fasteners that extend through spaced apart openings in the plate, particularly when each screw is perpendicular to the region of the plate surrounding it. Screws sufficiently short to avoid interfering with one another may not be long enough to assure a secure plate fixation. Further, the physician may encounter difficulties in positioning the plate if one of the vertebrae, due to a particular shape and orientation, cannot readily retain a perpendicularly inserted fastener.

There remains a need for greater flexibility in positioning and orienting the bone screws or fasteners, and for a simpler, more reliable means of counteracting the tendency of the bone screws to work loose after cervical plate fixation.

Therefore, it is an object of the present invention to provide a cervical plate and fixation system in which bone screws or other fasteners are more securely retained and less likely to work loose, without the need for auxiliary screws or other additional fixtures.

SUMMARY OF THE INVENTION

The invention provides a system for bone fixation comprising one or more plates comprising one or more fastener openings through which one or more fasteners can be passed to affix the plate to at least two vertebrae, the fastener openings passing from a top surface through the plate to a bottom surface, the bottom surface for positioning adjacent the vertebrae; and one or more blockers arranged adjacent the top surface, and having at least one end which protrude into a fastener opening, wherein the blockers are slidably attached so that they may be moved laterally perpendicular to a longitudinal axis of the plate capable of allowing the one or more fasteners to be installed into a respective vertebrae, and also capable of automatically preventing the one or more fasteners from substantially backing out of a respective fastener opening.

In one embodiment of the system of the invention, the system comprises two or more plates. Preferably, the two or more plates are slidably attached to each other, wherein the plates are free to move along a single axis of motion. In a further embodiment, the first plate of the two or more plates comprises a male component for being slidably received in a corresponding female receiving portion of a second plate.

In another embodiment of the system of the invention, the system comprises three or more plates. Preferably, the a first plate of the three or more plates comprises a male component for being slidably received in a corresponding female receiving portion of a second plate, wherein the second plate comprises a male and female portion received in a corresponding female receiving portion of a third plate and the male portion of the first plate.

In another embodiment of the system of the invention, the system further comprises one or more spring elements for enabling automatic return movement of a blocker to a home position. Preferably, the spring element is constructed from a material selected from the group consisting of nitinol, rubber and plastic.

In another embodiment of the system of the invention, the system comprises one plate.

In another embodiment of the system of the invention, the system comprises two or more plates attached in a manner that the two or more plates are slidably interlocked with one another.

In another embodiment of the system of the invention, the one or more fasteners are bone screws. Preferably the bone screws are self-drilling bone screws, self-tapping, polyaxial screws and/or rescue screws.

The invention also provides a method of increasing bone stability comprising affixing the system described above to the bone.

The invention also provides a method of increasing neck stability following cervical surgery comprising affixing the system described above to the cervical spine.

The invention also provides a dynamic plate system 17, described in FIG. 18, comprising a male/female plate 18 slidably joined to a male plate 11 and a female plate by interaction of a female connector component 14 on the male/female plate 18 and a male connector component 13 on the male plate 11 and interaction of a male connector component 13 on the male/female plate 18 and a female connector component 14 on the female plate, wherein each of the male/female plates 18, male plate 11 and female plate comprise at least one bone screw opening 3 and a recess 6 for housing the blocker 4.

The invention also provides a system for bone fixation comprising one or more plates comprising one or more bone screw openings through which one or more bone screws can be passed to affix the plate to at least two vertebrae, the bone screw openings passing from a top surface through the plate to a bottom surface, the bottom surface for positioning adjacent the vertebrae; and one or more blockers arranged adjacent the top surface, and having at least one end which protrude into a bone screw opening, wherein the blockers are slidably attached so that they may be moved laterally perpendicular to a longitudinal axis of the plate capable of allowing the one or more bone screws to be installed into a respective vertebrae, and also capable of automatically preventing the one or more bone screws from substantially backing out of a respective bone screw opening.

In one embodiment of the system of the invention, the system comprises two or more plates. Preferably, the two or more plates are slidably attached to each other, wherein the plates are free to move along a single axis of motion. In a further embodiment, a first plate of the two or more plates comprises a male component for being slidably received in a corresponding female receiving portion of a second plate.

In another embodiment of the system of the invention, the system comprises three or more plates. Preferably, the a first plate of the three or more plates comprises a male component for being slidably received in a corresponding female receiving portion of a second plate, wherein the second plate comprises a male and female portion received in a corresponding female receiving portion of a third plate and the male portion of the first plate.

In another embodiment of the system of the invention, the system further comprises one or more spring elements for enabling automatic return movement of a blocker to a home position. Preferably, the spring element is constructed from the group consisting of nitinol, rubber and plastic.

In another embodiment of the system of the invention, the system comprises one plate.

In another embodiment of the system of the invention, the system comprises two or more plates attached in a manner that the two or more plates are slidably interlocked with one another.

The invention also provides a method of increasing bone stability comprising affixing the system described immediately above to the bone.

The invention also provides a method of increasing neck stability following cervical surgery comprising affixing the system described immediately above to the cervical spine.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views.

DETAILED DESCRIPTION OF THE INVENTION

The apparatus of the invention is a system for bone fixation. Bone fixation is a technique wherein a plate is affixed to two or more bones so that the bones are held in one position relative to each other, or their freedom of motion is restricted in relation to each other in at least one axis of motion. This technique is often used on spinal vertebrae. More specifically, this technique is used on the cervical spine to increase neck stability following cervical surgery.

The apparatus of the invention comprises at least one plate which includes a plurality of bone screw openings (e.g., two or more) for receiving bone screws. Bone screws of any appropriate type and length may be used, including self-drilling screws, rescue screws, self-tapping, and polyaxial screws (i.e., screws which can be positioned in a plurality of angles relative to the bone screw receiving hole). In some embodiments, the bone screws pass through the openings in the plate, with at least one screw affixing an end or section of plate (or affixing an end/section of a first plate in the case of a two-plate system) to a first vertebrae, and at least one screw affixing another end or section of the plate (or affixing an end/section of a second plate in the case of a two-plate system) to a second vertebrae. Depending upon the length of the plate(s), more than two vertebrae may be affixed to portions of the plate(s). Optionally, the plate(s) is installed from the anterior aspect of the spine.

The plate system, according to some embodiments of the invention, may be static or dynamic. A static plate is one in which the vertebrae which are affixed to the plate do not move relative to one another—that is, the two (or more) vertebrae are in a fixed position, or the same spatial orientation with each other. In a dynamic plate system, two or more plates are used (as illustrated in the figures), which are slidably connected to one another, with each being affixed to a vertebrae. In a preferred embodiment, the two or more plates are slidably interlocked with one another. Preferably, the plates are allowed to move along one axis (e.g., the longitudinal axis of the combined plates), but prevent rotational movement between the plates. In one specific embodiment, the dynamic apparatus is arranged so that the one axis of movement for the plates is the same as the axis of the spine. This allows the vertebrae to move forward and backward in relation to each other, but does not allow them to twist in relation to each other.

Figure 1:
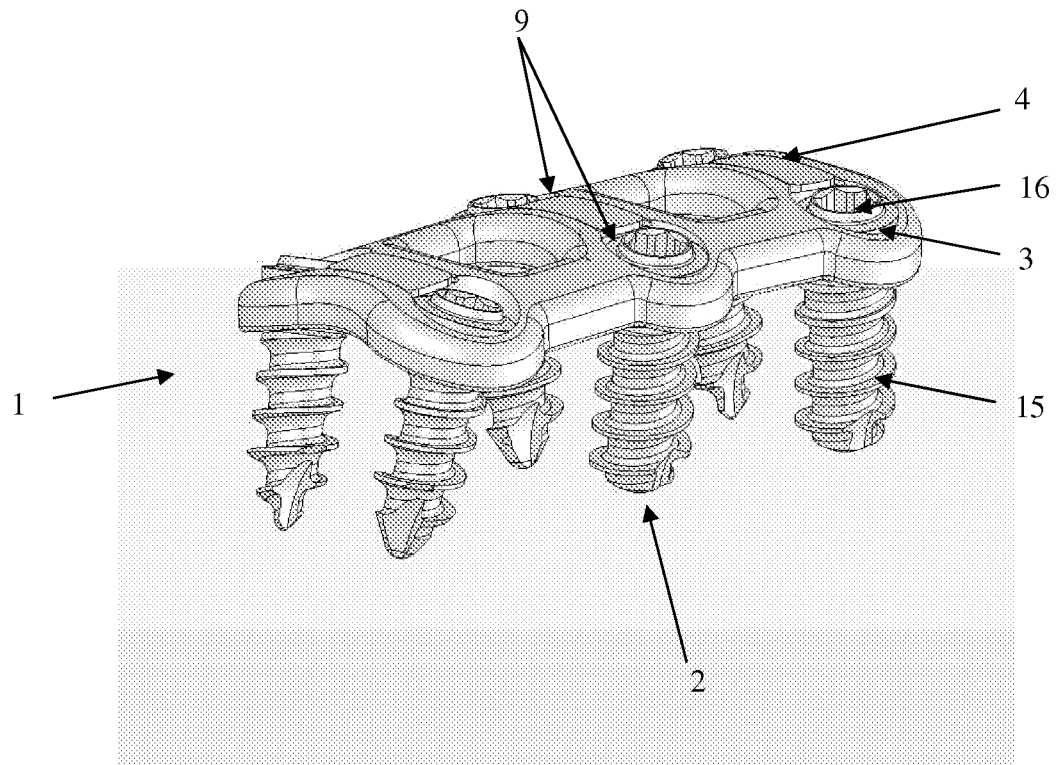
FIG. 1 illustrates a perspective view of a fully assembled static plate system according to some embodiments of the present invention.

Specific embodiments of the invention are illustrated in the Figures. For example, FIG. 1 shows a static plate system of the invention 1. Bone screws 2 are placed through bone screw openings 3 on the static plate system 1. The bone screw openings 3 are of a size so that the threads of the bone screws 15 may pass through the opening 3, but the head of the bone screw 16 may not pass entirely through the opening. However, the opening 3 is shaped so that a recess exists for the head of the bone screw 16 so it does not extend above the top surface of the static plate system 1. The blocker 4 is positioned on the static plate system 1 so as to prevent the bone screws 2 from backing out when the system is assembled as shown. The blocker 4 covers a portion of the head of the bone screws 16 with the ends of the blocker 9 thereby preventing the bone screws from backing out past the blocker 4, but not creating a necessity for the blocker to lock the bone screws in place.

Figure 2:
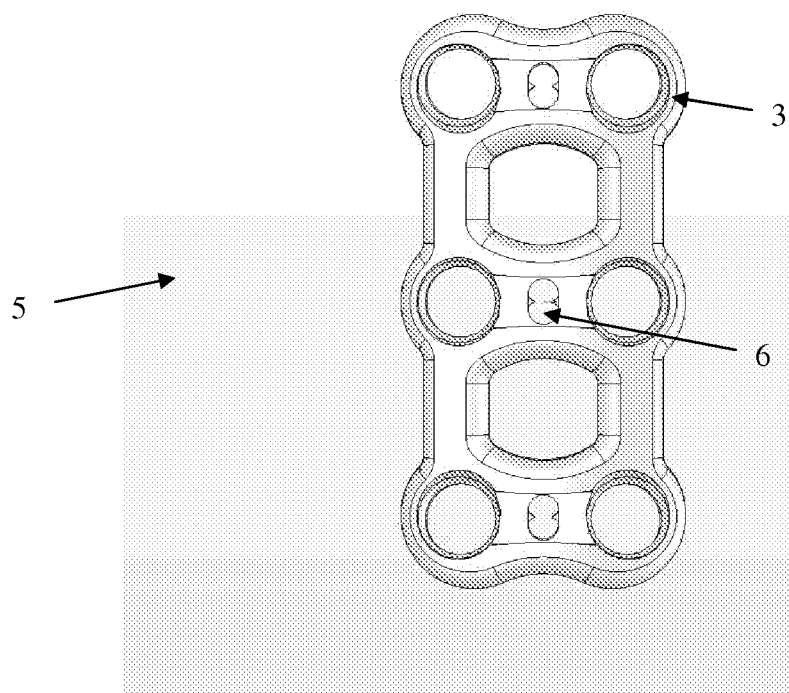
FIG. 2 illustrates a top view of a static plate according to some embodiments of the present invention.

FIG. 2 shows the plate of the static plate system 5 without the other parts of the assembly. This view is from the side of the plate that is positioned distal to the bone. Displayed are the bone screw openings 3 as well as the recess 6 for housing the blocker 4. Notice that the recess also comprises an opening that passed through to the opposite side of the plate 5.

Figure 3:
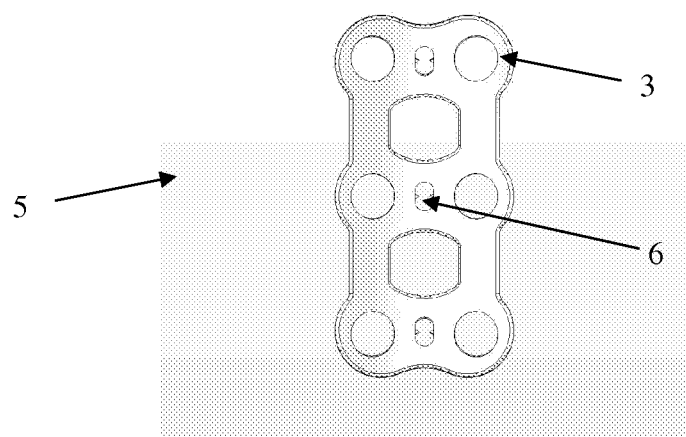
FIG. 3 illustrates a bottom view of a static plate according to some embodiments of the present invention.

FIG. 3 shows another view of the plate of the static plate system 5 without the other parts of the assembly. This view is from the side of the plate that is positioned proximal to the bone. The bone screw openings and recess 6 for housing the blocker 4 are again displayed. The opening that passes through the plate 5 in the recess 6 for housing the blocker 4 is also displayed.

Figure 4:
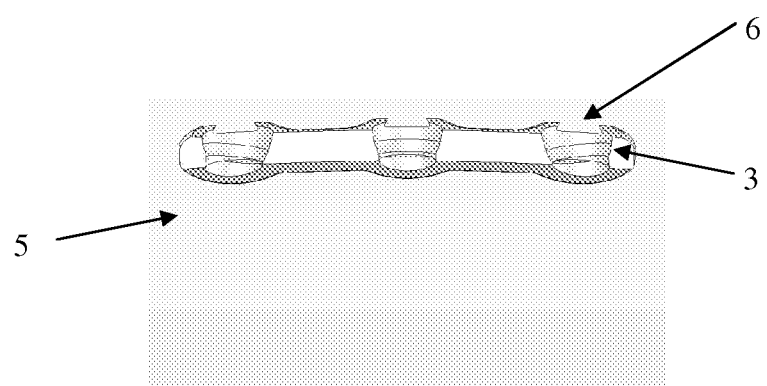
FIG. 4 illustrates a partial, cross-sectional, side view of a static plate according to some embodiments of the present invention.

FIG. 4 shows another view another view of the plate of the static plate system 5 without the other parts of the assembly. This view is from the side of the plate so that the side that is positioned distal to the bone is at the top and the proximal side at the bottom. The outline of the bone screw openings 3 are shown as well as the indentation formed by the recess 6 for housing the blocker 4.

Figure 5:
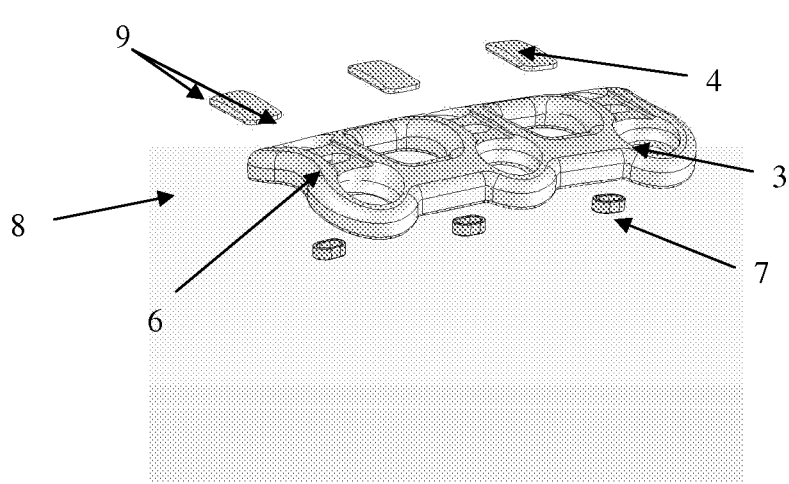
FIG. 5 illustrates an exploded, perspective view of a static plate system with slide/blocking elements and corresponding springs, according to some embodiments of the present invention.

FIG. 5 shows the assembly of the static plate system 8 without the bone screws 2. The blockers 4 are shown above the recess 6 for their housing. Also shown is the spring element 7. The spring element holds the blocker in place through the hole the passes through the plate at the housing for the blocker 6.

Figure 6:
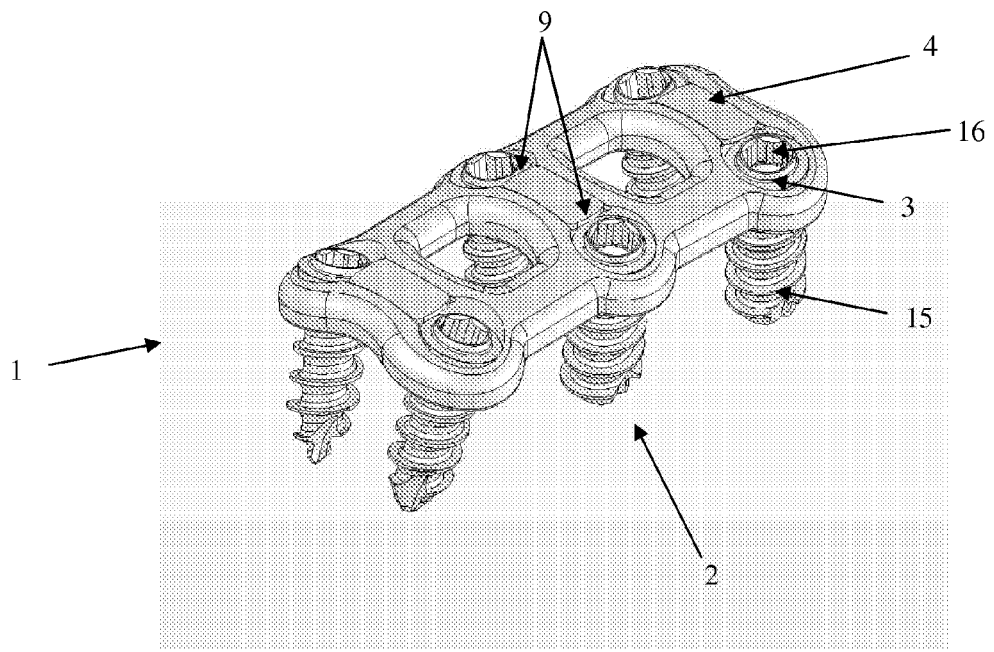
FIG. 6 illustrates another perspective view of a fully assembled static plate system according to some embodiments of the present invention.

FIG. 6 shows an alternative view of the assembled static plate system. Bone screws 2 are placed through bone screw openings 3 on the static plate system 1. The bone screw openings 3 are of a size so that the threads of the bone screws 15 may pass through the opening 3, but the head of the bone screw 16 may not pass entirely through the opening. However, the opening 3 is shaped so that a recess exists for the head of the bone screw 16 so it does not extend above the top surface of the static plate system 1. The blocker 4 is positioned on the static plate system 1 so as to prevent the bone screws 2 from backing out when the system is assembled as shown. The blocker 4 covers a portion of the head of the bone screws 16 with the ends of the blocker 9 thereby preventing the bone screws from backing out past the blocker 4, but not creating a necessity for the blocker to lock the bone screws in place.

Figure 7:
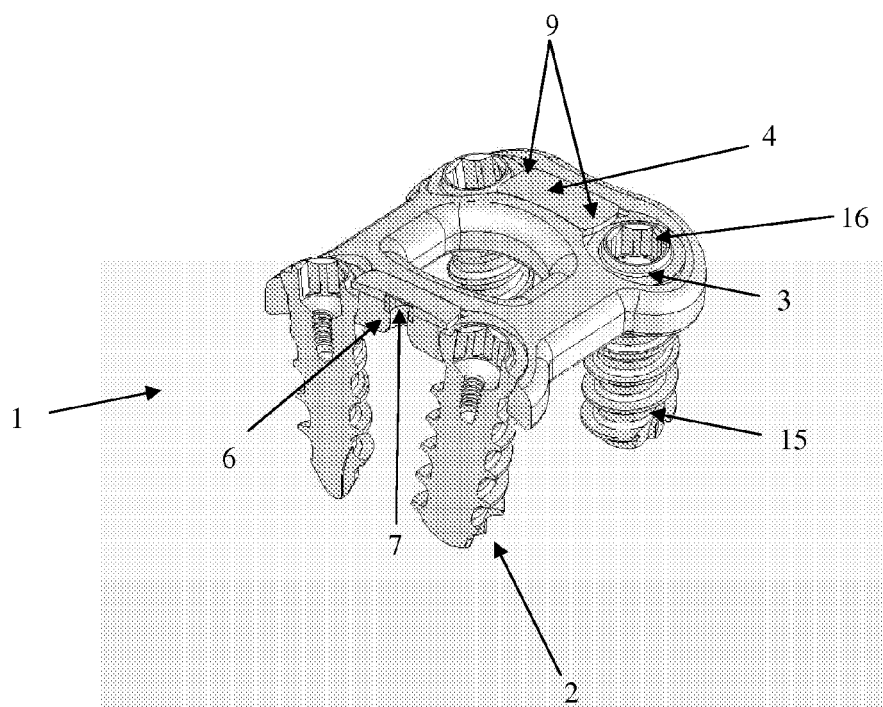
FIG. 7 illustrates a cutaway, perspective view of a fully assembled static plate system according to some embodiments of the present invention.

FIG. 7 shows a cross section of the static plate system 1. This cross section shows the elements described above for FIG. 6 but also shows the interaction of the spring element 7 and the blocker 4 at the recess housing the blocker 6. The dove-tail interlocking the of blocker 4 into the recess 6 for housing the blocker 4 is clearly shown. The spring element 7 sits above the triangular projections of the opening between the bone screws. Also, the bone screw opening 3 is shown in greater detail. The bone screw opening has a spherical portion that houses the head of the bone screw 16 holding the head of the bone screw 16 in place and allowing the threads of the bone screw 15 to pass through.

Figure 8:
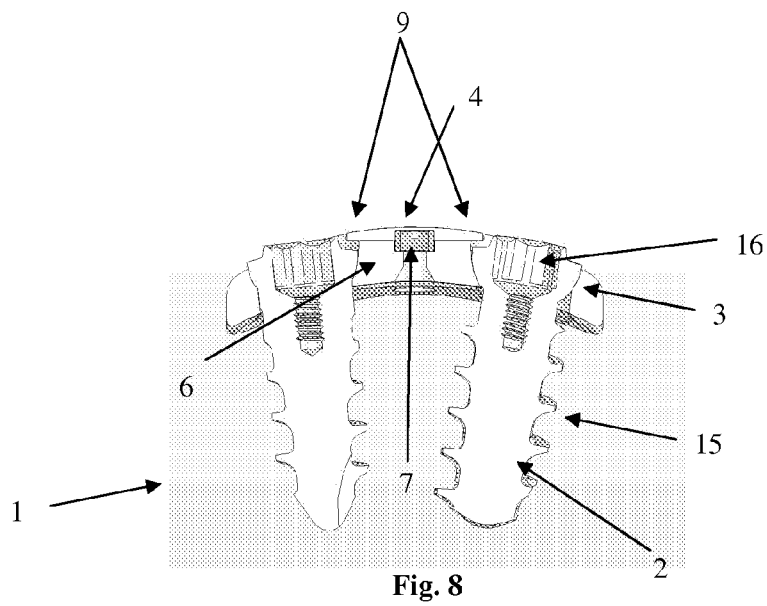
FIG. 8 illustrates a partial, cross-sectional view of a fully assembled static plate system according to some embodiments of the present invention.

FIG. 8 shows another cross section of the static plate system 1. This cross section shows the interaction of the spring element 7 and the blocker 4 at the recess 6 for housing the blocker 4. The dove-tail interlocking the of blocker 4 into the recess 6 for housing the blocker 4 is clearly shown. The spring element 7 sits above the triangular projections of the opening between the bone screws. Also, the bone screw opening 3 is shown in greater detail. The bone screw opening has a spherical portion that houses the head of the bone screw 16 holding the head of the bone screw 16 in place and allowing the threads of the bone screw 15 to pass through.

Figure 9:
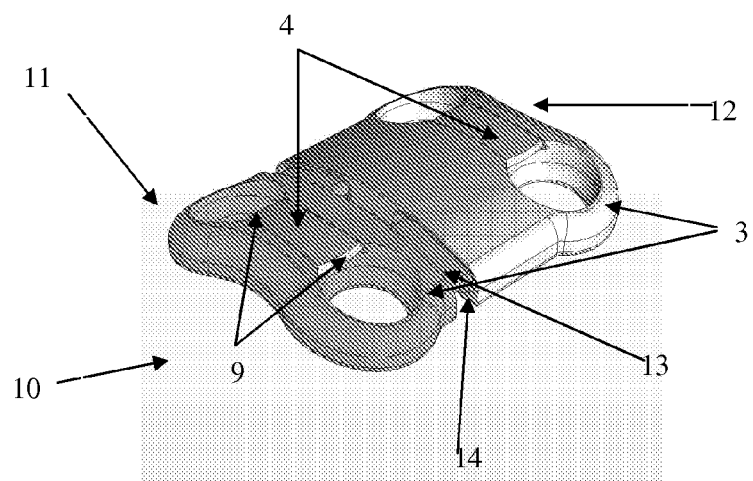
FIG. 9 illustrates another perspective view of an assembled dynamic plate system according to some embodiments of the present invention.

FIG. 9 shows two plates joined into the dynamic plate system of the invention 10. A male plate 11 with a male connecting component 13 is joined to a female plate 12 with a female connecting component 14. The blockers 4 are shown with their ends 9 overlapping the bone screw openings 3.

Figure 10:
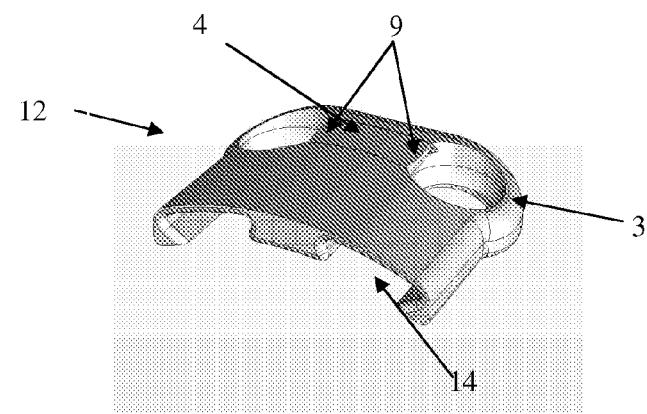
FIG. 10 illustrates a perspective view of a female component of a dynamic plate system according to some embodiments of the present invention.

FIG. 10 shows a female plate 12 for use with the dynamic plate system. The plate 12 is shown with the blocker 4 with its ends 9 overlapping the bone screw openings 3. The outline of the female connector component 14 is also shown.

Figure 11:
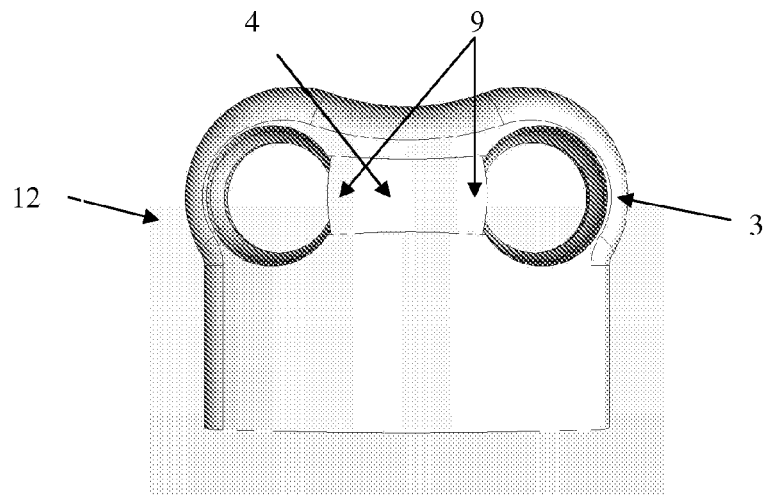
FIG. 11 illustrates a top view of a female component of a dynamic plate system according to some embodiments of the present invention.

FIG. 11 shows a top view of the female plate 12 for use with the dynamic plate system. The plate 12 is again shown with the blocker 4 with its ends 9 overlapping the bone screw openings 3.

Figure 12:
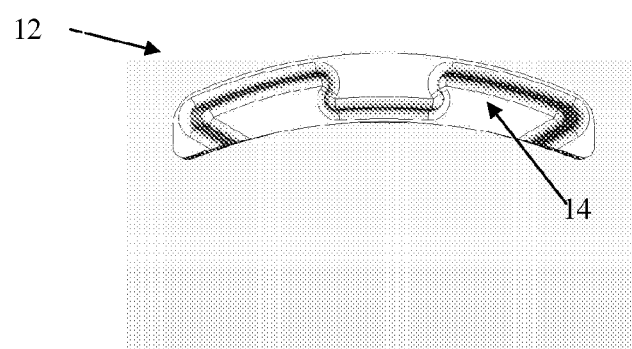
FIG. 12 illustrates a side view of a female component of a dynamic plate system according to some embodiments of the present invention.

FIG. 12 shows a side view of the female plate 12 with the female connector component 14 facing head on.

Figure 13:
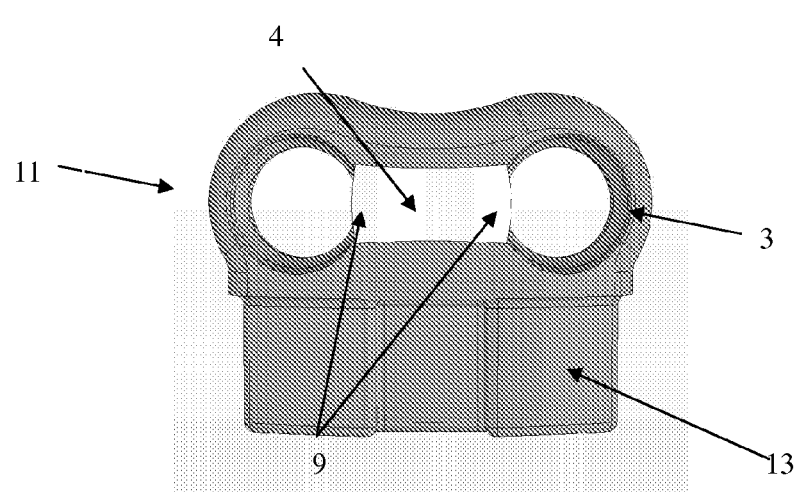
FIG. 13 illustrates a top view of a male component of a dynamic plate system according to some embodiments of the present invention.

FIG. 13 shows a top view of the male plate 11 for use with the dynamic plate system. The plate 11 is shown with the blocker 4 with its ends 9 overlapping the bone screw openings 3. The outline of the male connector component 13 is also shown.

Figure 14:
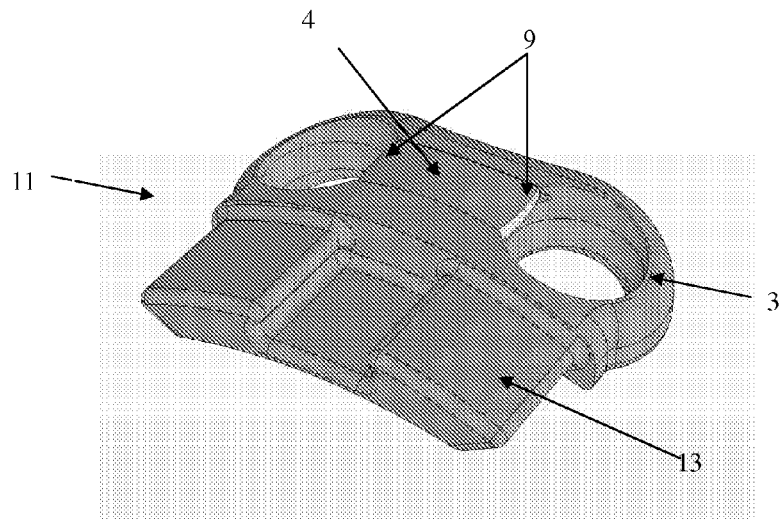
FIG. 14 illustrates a perspective view of a male component of a dynamic plate system according to some embodiments of the present invention.

FIG. 14 shows another view of the male plate 11 for use with the dynamic plate system. The plate 11 is shown with the blocker 4 with its ends 9 overlapping the bone screw openings 3. The male connector component 13 is also shown.

Figure 15:
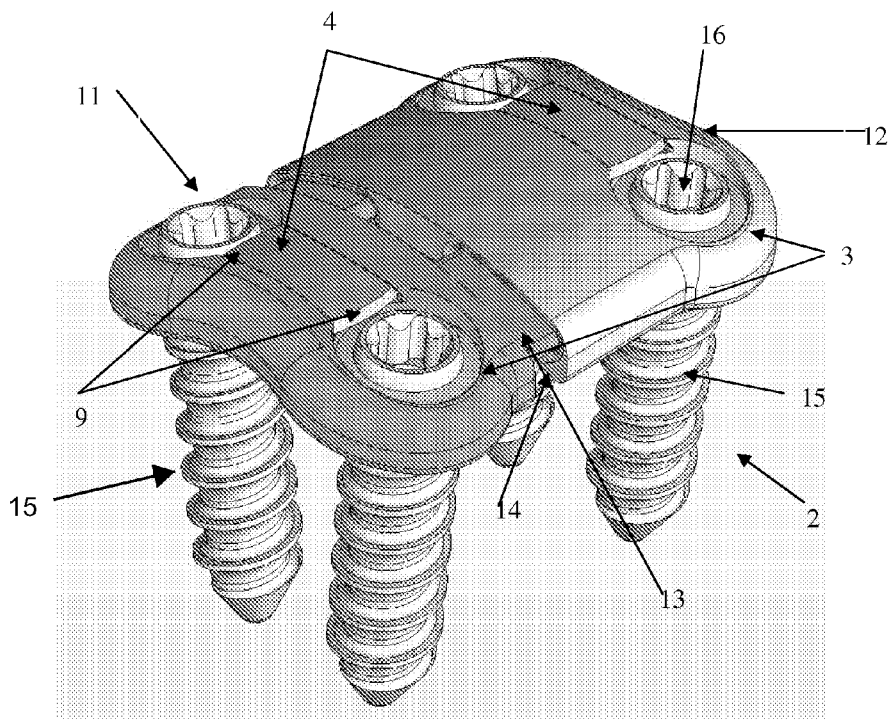
FIG. 15 illustrates a perspective view of a fully assembled dynamic plate system according to some embodiments of the present invention.

FIG. 15 shows the assembled dynamic plate system 15. Bone screws 2 are placed through bone screw openings 3 on the dynamic plate system 15. The bone screw openings 3 are of a size so that the threads of the bone screws 15 may pass through the opening 3, but the head of the bone screw 16 may not pass entirely through the opening. However, the opening 3 is shaped so that a recess exists for the head of the bone screw 16 so it does not extend above the top surface of the static plate system 1. The blocker 4 is positioned on the dynamic plate system 15 so as to prevent the bone screws 2 from backing out when the system is assembled as shown. The blocker 4 covers a portion of the head of the bone screws 16 with the ends of the blocker 9 thereby preventing the bone screws from backing out past the blocker 4, but not creating a necessity for the blocker to lock the bone screws in place. The male connector component 13 and female connector component 14 of the male plate 11 and female plate are interlocked.

Figure 16:
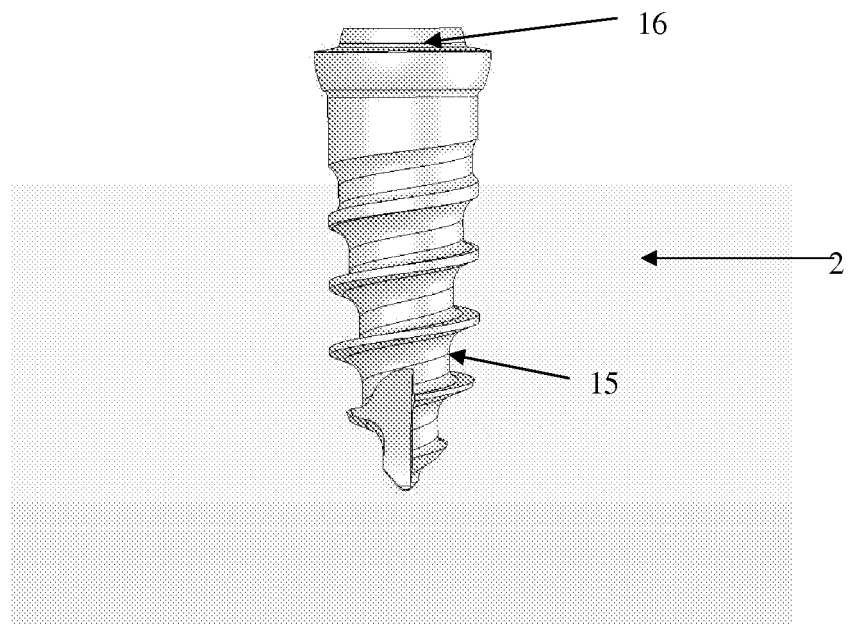
FIG. 16 illustrates a front view of a fixed, self-drilling screw for use in a plate system according to some embodiments of the present invention.

FIG. 16 a profile view of a bone screw. This bone screw is a fixed, self drilling screw for use with the plate systems of the invention. The head 16 and thread 15 portions of the screw are shown. This screw is a fixed orientation screw with a smaller head 16. This smaller head 16 in connection with the plate systems of the invention will allow this screw 2 to move about 9 degrees, which is more than the unfixed screw described below.

Figure 17:
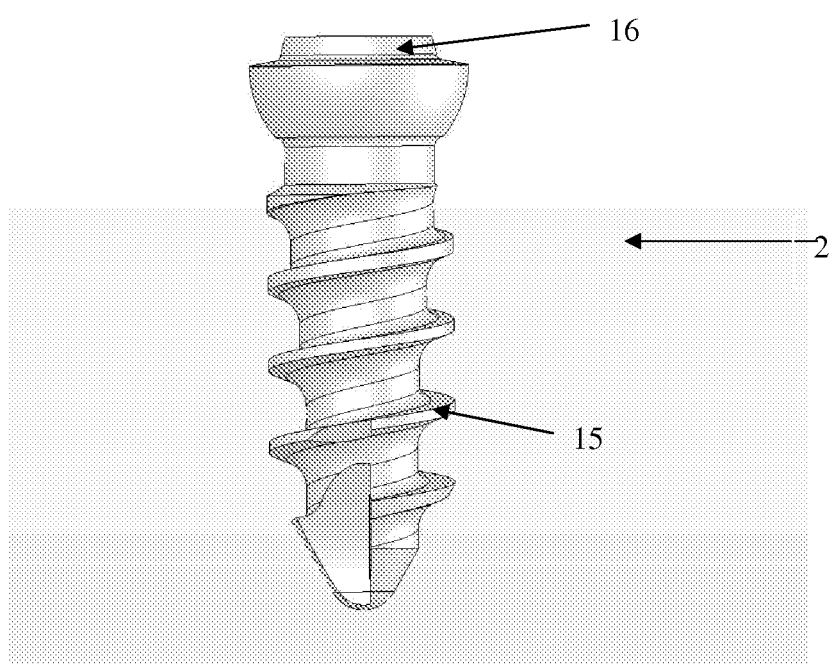
FIG. 17 illustrates a front view of a self-drilling screw for use in a plate system according to some embodiments of the present invention.

FIG. 17 a profile view of a bone screw. This bone screw is a self drilling screw for use with the plate systems of the invention. The head 16 and thread 15 portions of the screw are shown. This screw has a larger head 16. This larger head 16 in connection with the plate systems of the invention will only allow this screw 2 to move about 1.5 degrees, which is less than the fixed screw described above.

Figure 18:
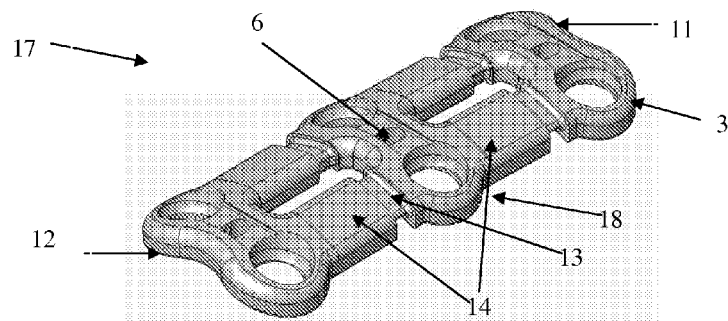
FIG. 18 illustrates a perspective view of a fully assembled dynamic plate system according to some embodiments of the present invention.

FIG. 18 shows the plates of a dynamic plate system 17 including a male/female plate 18. This view is from the side of the plate that is positioned distal to the bone. The male/female plate has a female connection component 14 and a male connection component 13 on opposite ends of the plate 18. This allows the male/female plate to attach to both a male plate 11 and a female plate 12 forming a larger dynamic plate system 17. Also displayed are the bone screw openings 3 as well as the recess 6 for housing the blocker 4. Notice that the recess also comprises an opening that passed through to the opposite side of the plates 11, 12, 18.

Figure 19:
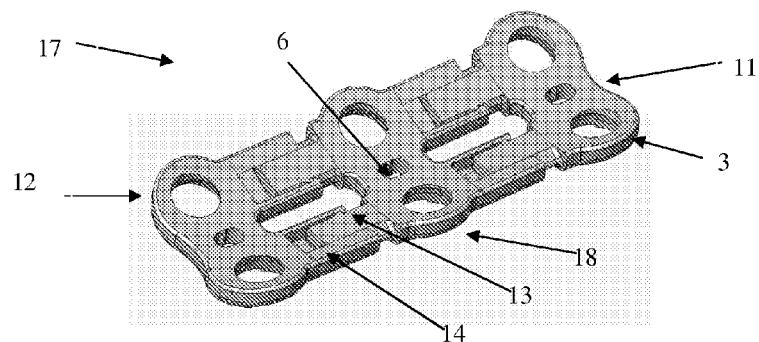
FIG. 19 illustrates a bottom perspective view of a fully assembled dynamic plate system according to some embodiments of the present invention.

FIG. 19 shows the plates of a dynamic plate system 17 from the opposite side. This view is from the side of the plate that is positioned proximal to the bone. The male/female plate 18, male plate 11, female plate 12, bone screw openings 3 and recess 6 for housing the blocker 4 are again displayed. The openings that passes through the plates 11, 12, 17 in the recess 6 for housing the blocker 4 are also displayed.

Figure 20:
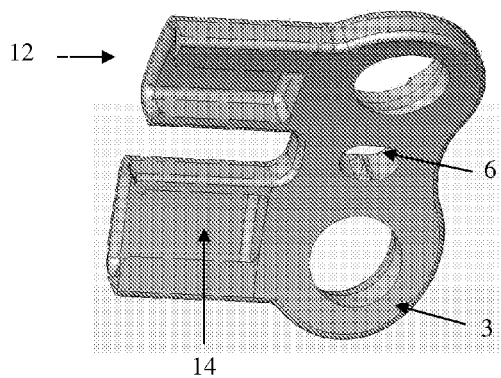
FIG. 20 illustrates a bottom perspective view of a female component of a dynamic plate system according to some embodiments of the present invention.

FIG. 20 shows a female plate 12 for use with the dynamic plate system. The plate 12 is shown so that the recess 6 for housing the blocker 4 is displayed with a hole passing through the plate 12. The bone screw holes are also displayed 3. The female connector component 14 is also shown.

Figure 21:
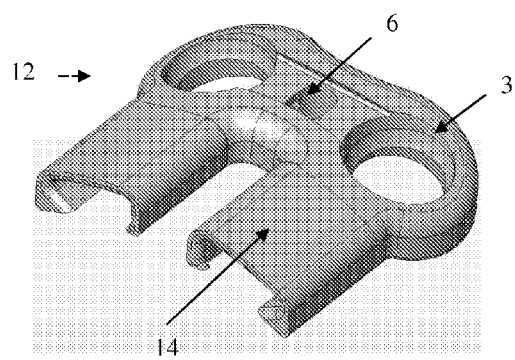
FIG. 21 illustrates a top perspective view of a female component of a dynamic plate system according to some embodiments of the present invention.

FIG. 21 shows the female plate 12 from a different perspective. Here, the female connector component 14 is more clearly visible.

Figure 22:
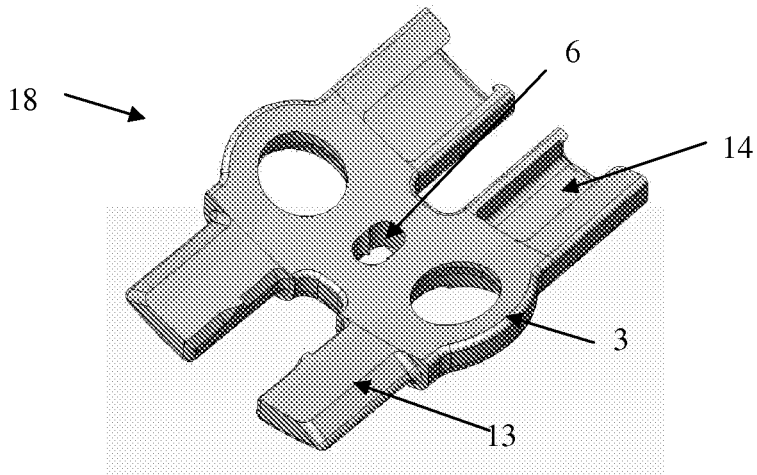
FIG. 22 illustrates a bottom perspective view of a male/female component of a dynamic plate system according to some embodiments of the present invention.

FIG. 22 shows the male/female plate 18. This plate has both a male connector component 13 and a female connector component 14. The plate 18 is shown so that the underside of the recess 6 for housing the blocker 4 is displayed with a hole passing through the plate 18. The bone screw holes are also displayed 3.

Figure 23:
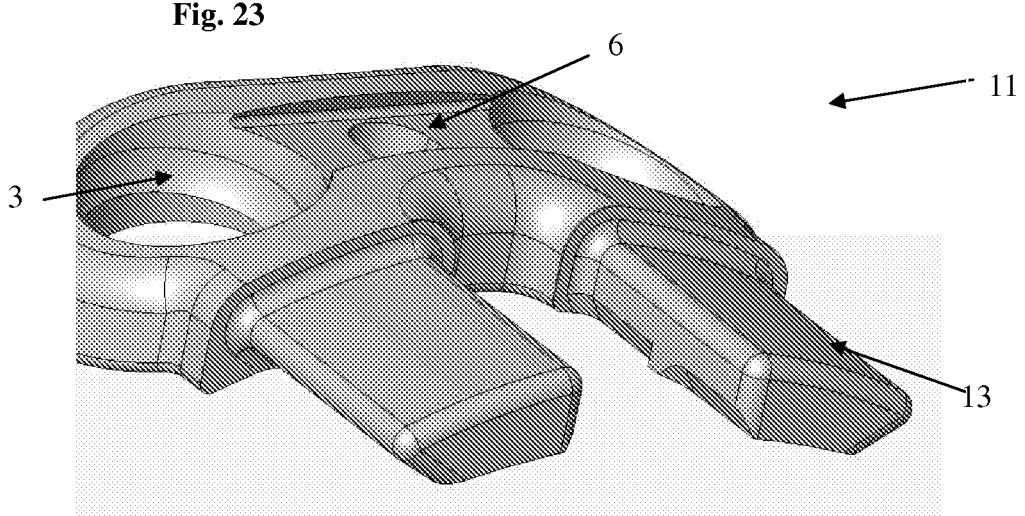
FIG. 23 illustrates a perspective view of a male component of a dynamic plate system according to some embodiments of the present invention.

FIG. 23 shows a view of the male plate 11 for use with the dynamic plate system. The plate 11 is shown so that the recess 6 for housing the blocker 4 is displayed with a hole passing through the plate 11. The bone screw holes are also displayed 3. The male connector component 13 is also shown.

Figure 24:
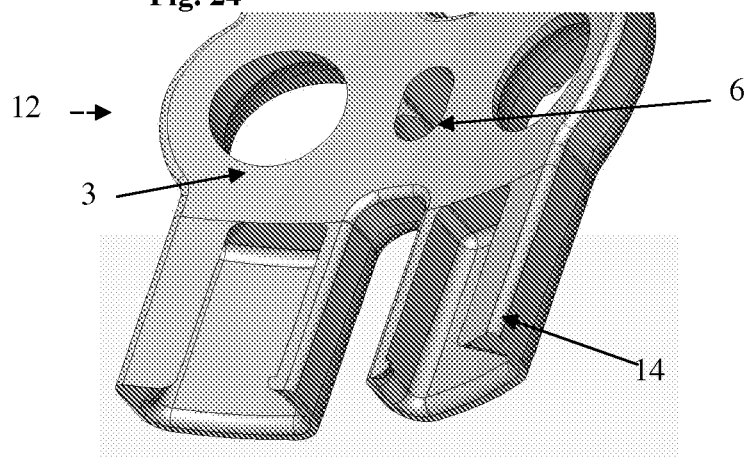
FIG. 24 illustrates a bottom perspective view of a female component of a dynamic plate system according to some embodiments of the present invention.

FIG. 24 shows a female plate 12 for use with the dynamic plate system. The plate 12 is shown so that the underside of the recess 6 for housing the blocker 4 is displayed with a hole passing through the plate 12. The bone screw holes are also displayed 3. The female connector component 14 is also shown.

Figure 25:
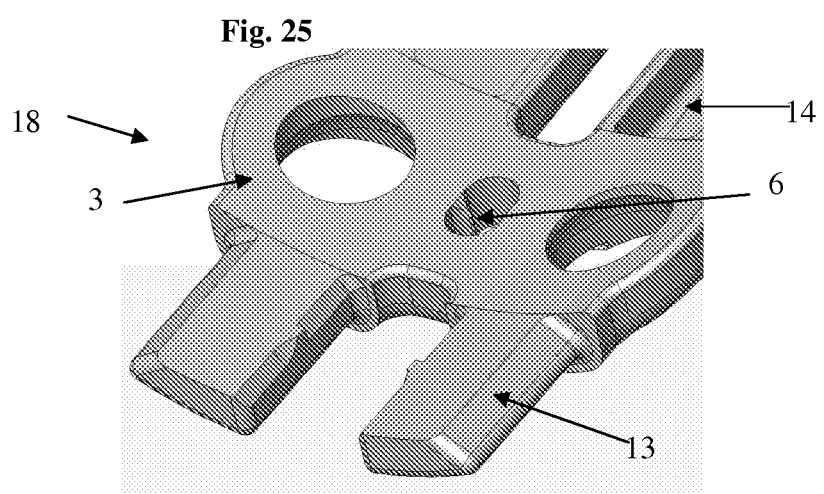
FIG. 25 illustrates a bottom perspective view of a male/female component of a dynamic plate system according to some embodiments of the present invention.

FIG. 25 shows another view of the male/female connector.

In one embodiment of the dynamic plate system, the plates are connected via male/female connectors, as shown in FIGS. 9, 15, 18 and 19. The male plate has a connecting element that fits inside a connecting element in a female plate. These elements allow the male and female plate to slide toward and away from each other along one axis of motion, but do not allow the plates to twist in relation to each other.

In another preferred embodiment of the invention, the apparatus further comprises blocking elements ("blockers"). These blocking elements prevent the fasteners from backing out of the positions where the fasteners are applied. The blocking elements are attached to the apparatus in a manner which allows the blocking elements to be easily displaced during the installation of the apparatus to the subject. Further, upon installation of the apparatus, the blocking elements return to their home state where they prevent the fasteners from backing out from where the fasteners were applied. In a preferred embodiment of the invention, the blocking elements do not lock the fasteners into place. The blocking elements allow the fasteners some room to back out, but will stop the fasteners after they have backed out a certain distance from where they have been installed. In another preferred embodiment, the blocking element is attached to the apparatus by a spring element. The spring element allows for the motion of the blocking element so that the bone screws of the apparatus of the invention may be installed, and then following the installation, the blocking element springs into place to prevent the backing out of the bone screws beyond they blocking element. In one aspect of this embodiment, the spring element is constructed of nitinol. In other aspects, the spring element is made of rubber or flexible plastic.

In another preferred embodiment, the blocking element, attached to the apparatus by the spring element is allowed to slide laterally by the spring element, but blocks the fasteners from backing out from where they were installed affixing the apparatus to the bone. Thus, the sliding/blocking element may be slid to the side for the installation procedure, but will still have sufficient tension to prevent the bone screws from backing out from where they were installed affixing the apparatus to the bone.

In another preferred embodiment, the blocking element operates so as to not rest on top of the fastener, for example, a bone screw while retaining the screws onto the plate. For example, the blocking element blocks only a portion of the screw from backing out from the bone but still allows access to the screw head. The blocking element may only block a small portion of the screw head and still retain the screw in the bone. Further the blocking element may act on a part of the screw other than the screw head, for example the threads of the screw.

In some of the illustrated embodiments, the spring element is placed in a receiving portion of a plate below the location of a sliding/blocking element. The sliding/blocking element, may be used to block the removal and/or rotation of bone screws, a respective head of such a screw being positioned adjacent an end of the slide. In particular, the end of the head preferably (in some embodiments) overlaps an edge of the head of a particular bone screw. In some embodiments, a single slide/blocking element is used to retain a pair of bone screws.

For example, as shown in FIG. 6, ends 9 of sliding/blocking elements 4, are situated on top of the heads of respective bone screws 16 of an assembled static plate system 1. In some embodiments, the spring element functions to preferably always apply a force to the sliding/blocking element so that it returns to a home location—that is, a state in which one or more ends of the sliding element overlap a respective head of a bone screw received in a bone screw opening in the static plate.

In another example, as shown in FIG. 15, ends 9 of sliding/blocking elements 4, are situated on top of the heads of respective bone screws 16 of assembled dynamic plate system 15. In some embodiments, the spring element functions to preferably always apply a force to the sliding/blocking element so that it returns to a home location—that is, a state in which one or more ends of the sliding element overlap a respective head of a bone screw received in a bone screw opening in the dynamic plate.

In a preferred embodiment of the static apparatus of the invention, upon a surgeon receiving the assembled plate, the sliding/blocking elements (as well as their corresponding springs) are fully assembled with the plate. A tip of a bone screw is inserted into a respective bone screw opening. As the bone screw is advanced, the end of the sliding/blocking element rides along the screw thread (for example), being moved out of the way, as the bone screw is screwed into the bone. The head of the bone screw also forces the sliding/blocking element out of the way. Upon the head of the screw passing the end of the sliding blocking element, the sliding/blocking element returns to the home location, where the end of the sliding/blocking element covers a portion of the edge of the head of the bone screw.

As can be seen in FIG. 15 as well, male component 13 of plate system 15, is received by female component 14. Other figures disclose the size and shape of the protruding members of the male component and corresponding receiving areas of the female component.

In some embodiments, the assembled dynamic plate system allows sliding relative movement in along one axis (typically parallel to the vertebral axis where the plate is used), while not allowing rotational movement between the two components.

One specific embodiment of the invention is the cervical plate system is shown below as FIGS. 5 and 8, which illustrate a perspective schematic view of the system (FIG. 5), and a cross-sectional view of the system, with bone screws installed (FIG. 8). Accordingly, the system is a static anterior cervical plate assembly and is available in a number of different lengths. Depending upon the length of the plate, a number of pairs of bone screw receiving holes are included to affix the plate to vertebrae. In one specific embodiment, if a cervical plate is used to attach to two vertebrae, the plate will include two pairs of bone screw holes, one for each vertebrae. The plate includes a concave longitudinal lower surface, for contacting the surface of the vertebrae.

Included with the system is an automatic, bone-screw blocking element ("Blocker") which is provided with the plate to keep bone screws from substantially backing out from the corresponding bone screw receiving holes. The Blocker is a generally rectangular member loosely positioned in a groove provided directly between a set of two individual bone screw receiving holes. The Blocker is able to easily slip back and forth in the groove with only slight pressure, and is designed to automatically transversely move across the plate in response to the head of a bone screw passing the Blocker. The plate is designed so that once a bone screw is seated in a bone screw hole, it can rotate and back-out slightly until it reaches the edge of the Blocker, as the Blocker does not "lock" the bone screws in place. As indicated, the Blocker moves automatically, along a straight transverse line, within the groove, laterally across the plate, in response to the interaction of the head of a bone screw as it passes the Blocker.

The automatic movement of the Blocker is facilitated by the inclusion of a spring member 7 beneath the Blocker. As shown in FIG. 8, a protrusion on either side of a recess located in the underside of the Blocker deflects the spring inward upon movement of the Blocker to a respective side of the plate. Specifically, when a bone screw is installed into a bone screw hole, the Blocker is in a home/final position for blocking the bone screws from substantially backing out of the bone screw holes. However, when the Blocker is in the home/final position, each bone screw can still be inserted into a corresponding bone screw hole and driven into the bone. Upon the head of the bone screw coming into contact with the Blocker, the Blocker automatically linearly displaces laterally, away from the head of the bone screw. Thereafter, as soon as the head of the bone screw passes the Blocker, the Blocker then automatically linearly displaces back to the home/final position. Accordingly, while the bone screw can rotate and back-out from within the bone screw hole, continued back-out is eliminated beyond the Blocker element.

In a preferred embodiment of the invention, the plates and bone screws of the apparatus are constructed of titanium. In another embodiment, the plates and bone screws are constructed of stainless steel. In another preferred embodiment, the apparatus of the invention is shaped to fit around the bones that are to be fixed. In one preferred embodiment, an apparatus of the invention has a concave shape to fit around vertebrae of a subject. In another preferred embodiment of the dynamic apparatus, each of the plates is shaped to fit on a bone to be fixed. Thus, the bones are allowed to move along one axis of range of motion, but is restricted in others.

I claim:

1. A system for bone fixation comprising:
   one or more plates comprising one or more pairs of fastener openings through which one or more fasteners can be passed to affix the plate to at least two vertebrae, the fastener openings passing from a top surface through the plate to a bottom surface, the bottom surface for positioning adjacent the vertebrae;
   one or more solid blockers within a recess arranged adjacent the top surface between pairs fastener openings, and each blocker having at least one end which protrudes into a respective opening of the pair of fastener openings; and
   one or more spring elements, each spring element coupled between a respective solid blocker and plate, the spring element configured to allow lateral movement of the solid blocker in a unitary fashion between the pair of fastener openings such that the solid blocker ends move into or out of the fastener openings; and
   an opening within the recess of the top surface that extends through the plate to the bottom surface of the plate, the opening configured to receive the spring element therethrough when the solid blocker covers the recess,
   wherein each of the solid blockers is slidably attached to the plate so that it may be moved in a unitary fashion laterally perpendicular to a longitudinal axis of the plate to allow the one or more fasteners to be installed into a respective vertebrae, and automatically returns to a locking position and to prevent the one or more fasteners from substantially backing out of a respective fastener opening.

2. The system of claim 1, wherein the system comprises two or more plates.

3. The system of claim 2, wherein the two or more plates are slidably attached to each other, wherein the plates are free to move along a single axis of motion.

4. The system of claim 3, wherein a first plate of the two or more plates comprises a male component for being slidably received in a corresponding female receiving portion of a second plate.

5. The system of claim 1, wherein the system comprises three or more plates.

6. The system of claim 5, wherein a first plate of the three or more plates comprises a male component for being slidably received in a corresponding female receiving portion of a second plate, wherein the second plate comprises a male and female portion received in a corresponding female receiving portion of a third plate and the male portion of the first plate.

7. The system of claim 1, wherein the spring element is constructed from a material selected from the group consisting of nitinol, rubber and plastic.

8. The system of claim 1, wherein the system comprises one plate.

9. The system of claim 1, wherein the system comprises two or more plates attached in a manner that the two or more plates are slidably interlocked with one another.

10. The system of claim 1, wherein the one or more fasteners are bone screws.

11. The system of claim 10, wherein the bone screws are self-drilling bone screws.

12. The system of claim 10, wherein the bone screws are self-tapping, polyaxial screws.

13. The system of claim 10, wherein the bone screws are rescue screws.

14. A method of increasing bone stability comprising affixing the system of claim 1 to the bone.

15. A method of increasing neck stability following cervical surgery comprising affixing the system of claim 1 to the cervical spine.

16. The system of claim 1, wherein the spring element is configured for enabling automatic return movement of the blocker to the locking position.

* * * * *